(12) United States Patent
Wilmink

(10) Patent No.: US 8,689,931 B2
(45) Date of Patent: Apr. 8, 2014

(54) EAR PROTECTOR WITH A SOUND DAMPING FILTER, SOUND DAMPING FILTER FOR SUCH AN EAR PROTECTOR AS WELL AS METHOD FOR MANUFACTURING A SOUND DAMPING FILTER FOR SUCH AN EAR PROTECTOR

(75) Inventor: Engbert Wilmink, Delft (NL)

(73) Assignee: Dynamic Ear Company B.V. (NL)

( * ) Notice: Subject to any disclaimer, the term of this patent is extended or adjusted under 35 U.S.C. 154(b) by 0 days.

(21) Appl. No.: 13/516,298

(22) PCT Filed: Dec. 7, 2010

(86) PCT No.: PCT/NL2010/050827
§ 371 (c)(1),
(2), (4) Date: Jul. 20, 2012

(87) PCT Pub. No.: WO2011/078659
PCT Pub. Date: Jun. 30, 2011

(65) Prior Publication Data
US 2013/0126262 A1    May 23, 2013

(30) Foreign Application Priority Data

Dec. 22, 2009  (NL) ..................... 2004004

(51) Int. Cl.
*A61F 11/06* (2006.01)
*H04R 1/10* (2006.01)
*H04R 25/00* (2006.01)

(52) U.S. Cl.
USPC ............... 181/135; 264/279; 381/72; 381/74; 381/325

(58) Field of Classification Search
USPC ............. 181/135; 128/846; 264/279; 381/74, 381/325
See application file for complete search history.

(56) References Cited

U.S. PATENT DOCUMENTS

| 4,344,425 | A | * | 8/1982 | Strauss | 128/864 |
| 4,465,159 | A | * | 8/1984 | Stallings | 181/129 |
| 4,540,063 | A | * | 9/1985 | Ochi et al. | 181/135 |
| 4,856,118 | A | * | 8/1989 | Sapiejewski | 2/209 |
| 4,896,679 | A | * | 1/1990 | St. Pierre | 128/865 |
| 5,488,961 | A | * | 2/1996 | Adams | 128/864 |
| 6,134,333 | A | * | 10/2000 | Flagler | 381/325 |

(Continued)

FOREIGN PATENT DOCUMENTS

| CA | 2382309 A1 | 3/2001 |
| DE | 1120632 B | 12/1961 |

(Continued)

OTHER PUBLICATIONS

International Search Report, PCT/NL2010/050827, Mailing date: Apr. 21, 2011.

(Continued)

*Primary Examiner* — David Warren
*Assistant Examiner* — Christina Russell
(74) *Attorney, Agent, or Firm* — Banner & Witcoff, Ltd.

(57) ABSTRACT

An ear protector (1) with a sound damping filter (3), comprises a membrane (5). The membrane is composed of a material that permits the transmission of air and water vapor with respect to the ear from the into the outside of the ear protector, the membrane is pre stressed mounted in the filter, enabling a bigger surface and hence bigger air and water transport at same sound attenuation.

17 Claims, 5 Drawing Sheets

(56) References Cited

U.S. PATENT DOCUMENTS

| | | | |
|---|---|---|---|
| 6,152,137 A * | 11/2000 | Schwartz et al. | 128/846 |
| 6,408,981 B1 * | 6/2002 | Smith et al. | 181/126 |
| 6,691,822 B2 * | 2/2004 | Meussen et al. | 181/135 |
| 6,790,926 B1 * | 9/2004 | Spijkers et al. | 528/79 |
| 7,185,655 B1 * | 3/2007 | Redon | 128/864 |
| 7,313,245 B1 * | 12/2007 | Shennib | 381/325 |
| 7,664,282 B2 * | 2/2010 | Urso et al. | 381/328 |
| 8,201,561 B2 * | 6/2012 | Blanchard | 128/864 |
| 8,419,637 B2 * | 4/2013 | Nielsen et al. | 600/301 |
| 2002/0179365 A1 * | 12/2002 | Meussen et al. | 181/135 |
| 2003/0159878 A1 * | 8/2003 | Hakansson et al. | 181/135 |
| 2007/0086599 A1 * | 4/2007 | Wilmink | 381/74 |
| 2008/0187151 A1 * | 8/2008 | McClenon | 381/74 |
| 2009/0220103 A1 * | 9/2009 | Wilmink | 381/74 |
| 2009/0238374 A1 * | 9/2009 | Keady | 381/72 |
| 2011/0019851 A1 * | 1/2011 | Michel et al. | 381/326 |
| 2011/0235843 A1 * | 9/2011 | Keady et al. | 381/380 |
| 2012/0103346 A1 * | 5/2012 | Keady | 128/865 |
| 2012/0305329 A1 * | 12/2012 | Keady et al. | 181/135 |

FOREIGN PATENT DOCUMENTS

| | | |
|---|---|---|
| EP | 1078615 A1 | 2/2001 |
| EP | 1099433 A3 | 12/2002 |
| WO | 01/76520 A1 | 10/2001 |

OTHER PUBLICATIONS

Novelty Search Report—NL 2004004—Date of completion: Aug. 1, 2010.

* cited by examiner

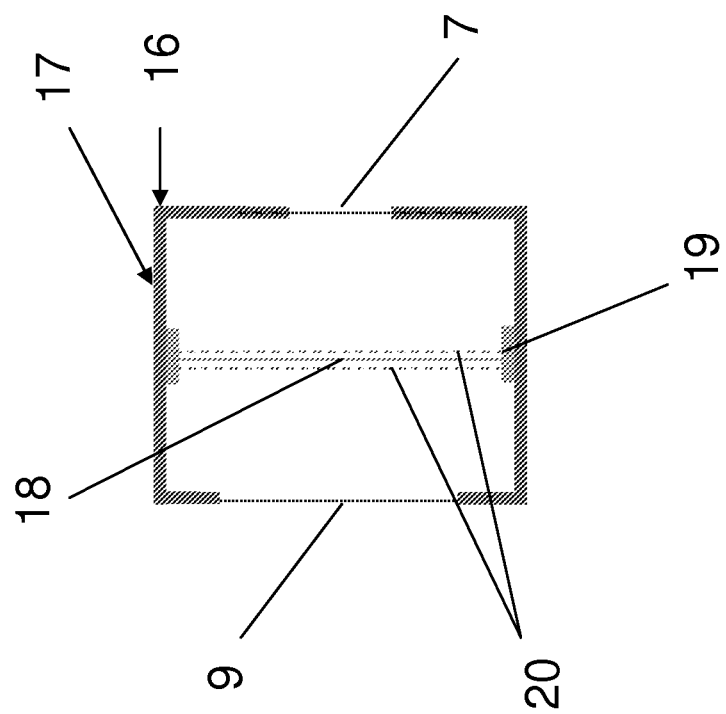

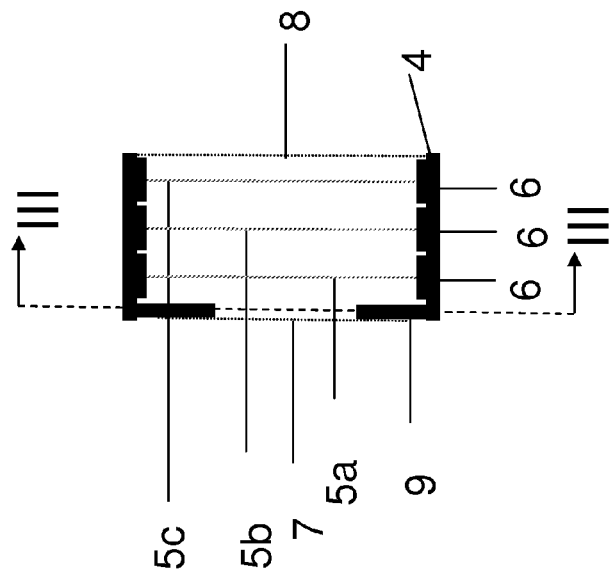
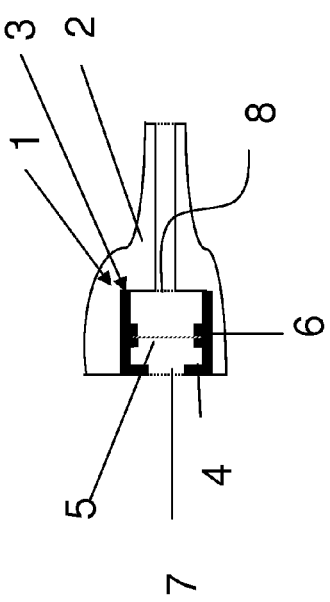
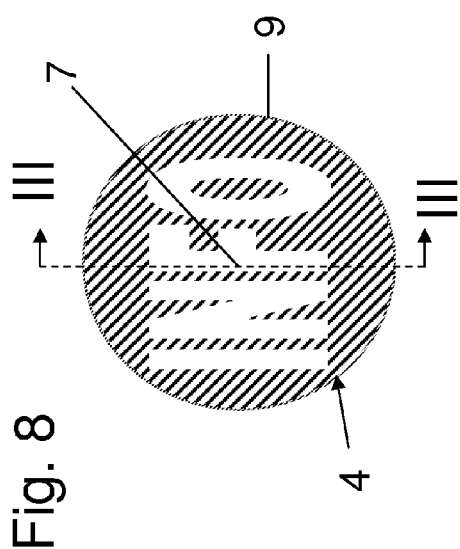

EAR PROTECTOR WITH A SOUND DAMPING FILTER, SOUND DAMPING FILTER FOR SUCH AN EAR PROTECTOR AS WELL AS METHOD FOR MANUFACTURING A SOUND DAMPING FILTER FOR SUCH AN EAR PROTECTOR

CROSS-REFERENCE TO RELATED APPLICATIONS

This application is a U.S. National Stage application under 35 U.S.C. §371 of International Application PCT/NL2010/050827 (published as WO 2011/078659 A1), filed Dec. 7, 2010 which claims priority to Application NL 2004004, filed Dec. 22, 2009. Benefit of the filing date of each of these prior applications is hereby claimed. Each of these prior applications is hereby incorporated by reference in its entirety.

FIELD OF INVENTION

The invention relates to ear protectors with a sound filter.

DESCRIPTION OF PRIOR ART

The invention relates to an ear protector with a sound damping filter, comprising a membrane composed of a material for permitting the transmission of air with respect to the ear from the outside to the inside of the ear protector.

Such an ear protector with sound damping filter is disclosed in EP 1 046 382 A1 and provides with its perforated membrane a ventilation of the ear canal. Ventilation of the ear canal is important for the drain of perspiration and the reduction of inflammations. The sound damping characteristics of the sound damping filter in this known ear protector depend on the kind of material of the membrane, its dimensions and the number and dimensions of the perforations. However, this known ear protector with its perforated membrane cannot prevent penetration of water in the ear canal and is not suitable for example for people with openings in the eardrum.

An ear protector offering a watertight seal as well as a ventilation of the ear canal is disclosed in U.S. Pat. No. 5,488,961A. This known ear protector is developed for swimming, diving and other water related activities and provides with its micro-porous membrane a watertight seal of the ear. Its membrane is missing the function of a sound damping filter. The microscopic pores of this known ear protector that let air and water vapour pass through, yet have such low surface energy that the surface tension of any (liquid) water in contact remains too high to allow it to squeeze through the pores. Microporous membranes have traditionally been let down by the contamination of their pores which significantly degrades the moisture transfer through the membrane and commonly also have poorer adhesion to fabrics making them more susceptible to de-lamination.

It is an object of the invention to provide an ear protector with sound damping filter having both a good moister transfer through the membrane and a good sound attenuation.

DISCLOSURE OF THE INVENTION

According to the invention the membrane is composed of a material for permitting the transmission of air and water vapour with respect to the ear from the inside to the outside of the ear protector, the membrane being pre-stressed mounted in the sound damping filter, enabling a bigger membrane surface and hence bigger air and water vapour transport at the same sound attenuation.

This non-porous monolithic membrane is closed (i.e. it has no pores), no water can get in from the outside, but water vapour molecules are transported through the membrane from the inside to the outside of the ear protector by way of an absorption and evaporation process. This moisture transfer through the membrane is referred to as "breathability."

Preferably, the membrane being pre-stressed mounted in the sound damping filter, enabling a 100-250% bigger membrane surface, preferably a 150-200% bigger surface, with respect to the original surface. With this bigger surface the damping characteristics of the sound damping filter are fixed on the required level.

Preferably, the non-porous material comprises polyester for molecular strength and polyether to transport water vapour molecules. Such a membrane is $1/100$ mm thick, translucent, stretchable with good stretch recovery, completely recyclable and relatively environmentally friendly.

Preferably, the non-porous material comprises a thermoplastic polyurethane. This material has a good water vapour permeability, but also high tackiness.

Preferably the membrane is composed of non-porous material enabling water vapour molecules to be transported through the membrane from the inside to the outside of the ear protector by way of absorption and evaporation process and preventing the transmission of water from the outside to the inside of the ear protector.

Further advantageous embodiments of the invention are described in other dependent claims.

According to another aspect the invention relates to one of the methods for manufacturing a sound damping filter for an ear protector, said sound damping filter comprising a membrane composed of material permitting with respect to the ear from the inside to the outside of the ear protector the transmission of water vapour and of air, wherein the method comprising following steps: the membrane is pre-stressed with a defined force, the membrane is placed pre-stressed in a mould, and by injection moulding a support is joined to the membrane.

This provides a method by which the required damping characteristics of the sound damping filter, given a certain desired acoustical transfer function, can be fixed during manufacturing.

BRIEF DESCRIPTION OF THE DRAWINGS

The invention will be further elucidated on the basis of embodiments represented in the drawing, in which:

FIG. 3 shows on enlarged scale a sectional view of a sound damping filter of an ear protector according to a third embodiment of the invention.

FIG. 6 shows an alternative embodiment of an ear protector.

FIGS. 7-10 show alternative embodiments of sound damping filters.

DESCRIPTION OF THE EMBODIMENTS

Figure 1:
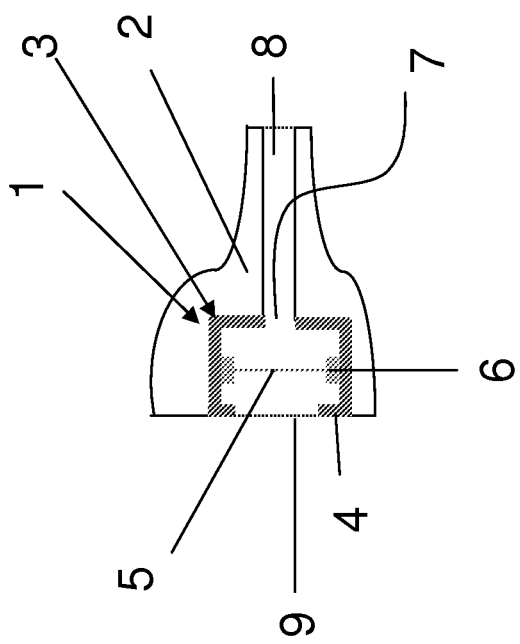
FIG. 1 shows a sectional view of an ear protector with a sound damping filter according to a first embodiment of the invention.

An ear protector 1, shown in FIG. 1 comprises a custom earpiece 2, in which a sound damping filter 3 is mounted. This filter 3 comprises a filter housing 4 with a membrane 5, mounted on a membrane support 6. This support has standardized dimensions and is mounted in a sound channel 7 of the ear protector, connecting the inside 8 and outside 9 of the of the ear protector. The sound damping filter 3 may be a separate construction element, so that it is exchangeable. The membrane 5 is composed of non-porous material enabling water vapour molecules to be transported through the membrane from the inside 8 to the outside 9 of the ear protector 1 by way of absorption and evaporation process and preventing the transmission of water from the outside to the inside of the ear protector. This moisture transfer through the membrane is what is referred to as "breathability." Preferably the membrane 5 is composed of non-porous monolitic material that comprises a thermoplastic polyurethane. Such water vapour permeable thermoplastic polyurethane films are disclosed in U.S. Pat. No. 6,790,926 B1. An alternative preferred material of the monolithic, non-porous membrane is composed of polyester for molecular strength and polyether to transport water vapour molecules. An example of this material of SympaTex, a TM of Sympatex Technologies, for a closed membrane is made of hydrophilic polyether-ester block copolymer, which is closed (i.e. it has no pores). This co-polymer consists of polyester for molecular strength, and polyether to transport water molecules. The membrane is $1/100$ mm thick, translucent, and stretchable with good stretch recovery. The SympaTex material is completely recyclable and relatively environmentally friendly.

Figure 2:
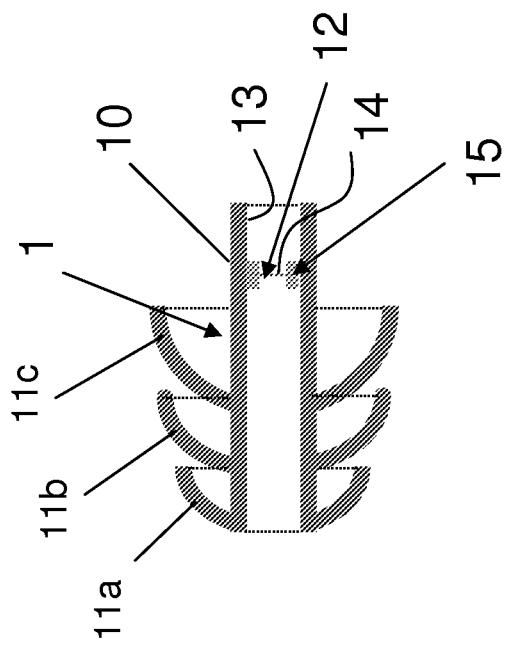
FIG. 2 shows a sectional view of an ear protector with a sound damping filter according to a second embodiment of the invention.

In FIG. 2 is shown a second embodiment of the ear protector 1, comprising a universal earpiece 10 that is sealed to the ear by means of three flanges 11a, 11b and 11c. In the ear protector a sound damping filter 12 is mounted, comprising a sound channel 13, which also is a filter housing for a membrane 14, mounted on a membrane support 15. The membrane 14 is composed of a non-porous material with same composition and same "breathability" characteristics as the membrane 5 in FIG. 1.

FIG. 3 shows in a third embodiment of the ear protector 1 a sound damping filter 16 with a filter housing 17 comprising a membrane 18, mounted on a membrane support 19. The membrane 18 is composed of a non-porous material with same composition and same "breathability" characteristics as the membrane 5 in FIG. 1. This filter housing 17 has same dimensions and characteristics as the filter housing 4 and is mounted in the custom earpiece 2. The support 19 carries membrane deflection limiters 20, located at both sides of the membrane 18, each comprising an impulse blocker mesh. This support 19 has standardized dimensions and is mounted in the sound channel 7 of the ear protector, connecting the inside 8 and outside 9 of the of the ear protector. These impulse blocker mesh are limiting the deflections of the membrane due to overpressure and under-pressure in the sound channel. This limitation of the deflection stops a pressure wave in the sound channel 7 on an effective way.

In an alternative of the embodiment in accordance with FIG. 3 (not shown) the deflection limiters are open in a central area, but closed in their main surface. Due to deflection of the membrane, the central opening in the respective deflection limiter is closed. These deflection limiters have a very effective sound damping working for heavy acoustic waves.

For manufacturing of the sound damping filter 3, 12, 16 the membrane 5, 14 and 18 can be mounted on the membrane support by different methods like by gluing, cementing, etc. During an advantageous method for manufacturing the sound damping filter in accordance with the invention the membrane 5, 14, 18 is pre-stressed with a defined force, the membrane is placed pre-stressed in a mould, and by injection molding a support is joined to the membrane. With this method the membrane becomes a 100-250% bigger surface, preferably a 150-200% bigger surface with respect to the original surface. Thus the required damping characteristics of the sound damping filter, given a certain desired acoustical transmission, can be fixed during manufacturing. The membrane 5, 14, 18 composed of non-porous material such as a thermoplastic polyurethane is very suitable for this method.

Alternatively, the sound damping filter 3, 12, 16 may comprise a porous membrane, composed of a material for permitting the transmission of air and water vapour with respect to the ear from the inside to the outside of the ear protector. In this embodiment the membrane is pre-stressed enabling a bigger membrane surface and hence bigger air and water vapour transport at the same sound attenuation.

In an advantageous alternative method for manufacturing of the sound damping filter with a membrane composed of porous or non-porous material the method comprises the steps of joining the membrane 5, 14, 18 to a support and pre-stressing the membrane by applying a specific treatment, such as heattreatment, to introduce the required stress in the membrane.

In yet another advantageous alternative method for manufacturing of the sound damping filter with a membrane composed of porous or non-porous material the method comprises the steps of joining the membrane 5, 14, 18 to a support and pre-stressing the membrane by applying a defined deformation of the membrane to introduce a required stress in the membrane upon assembly of the support of the membrane with another part of the ear protector, such as a housing of the filter or another support of the filter.

Figure 5:
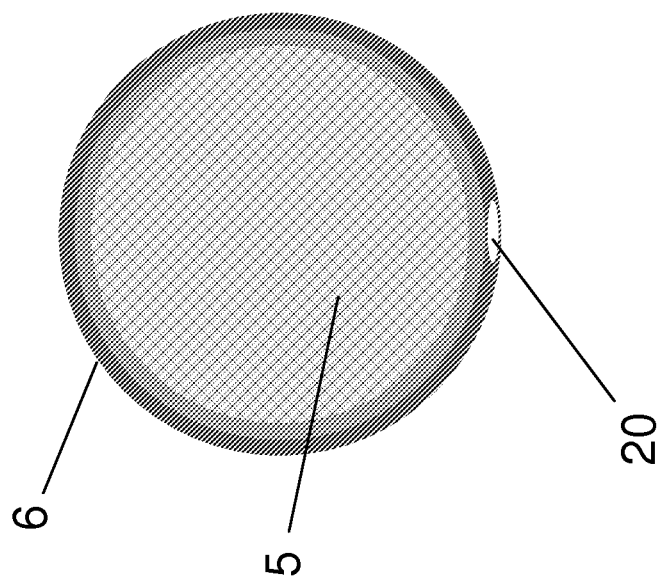
FIG. 5 shows a sectional view along lines V-V through a wall of the filter housing of the damping filter in FIG. 4.
Figure 4:
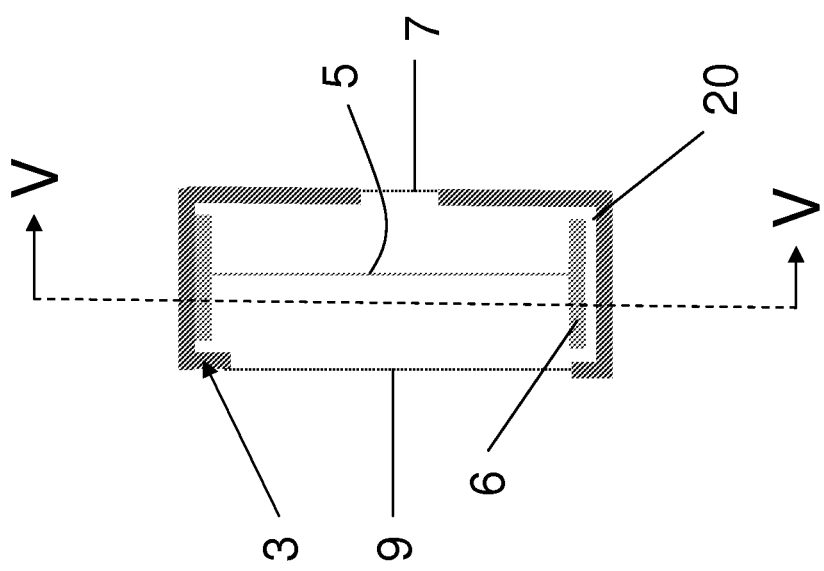
FIG. 4 shows on enlarged scale a sectional view of the sound damping filter of the ear protector of FIG. 1 with a first and a second acoustic channel according to a fourth embodiment of the invention.
Figure 10:
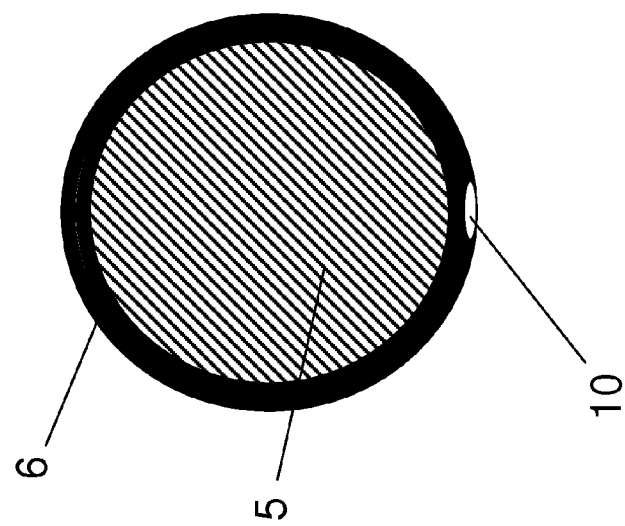
Figure 9:
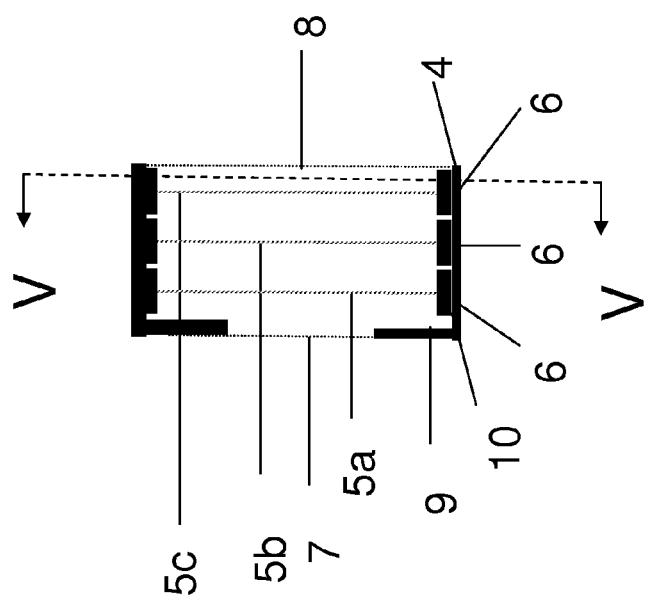

As shown in FIGS. 4 and 5 in yet another embodiment of the invention the filter 3 comprises beside the first sound channel 7 also a second sound, acoustic channel extending from one side 8 of the filter to the other side 9. The first channel extends from the side 7 of the filter through the membrane 5 to the other side 8. The second channel may pass an opening 20 in the housing 4, or alternatively (not shown) an opening in an edge of the membrane 5. Said second acoustic channel being designed for less attenuation of low frequencies. For adjusting the damping characteristics, the dimension of the second acoustic channel can be varied by rotation of the housing 4 of the filter 3 with respect to the membrane 5. Preferably also the second channel is closed by material, enabling water vapour molecules to be transported through the channel from the inside 8 to the outside 9 and preventing the transmission of water from the outside to the inside. FIG. 6 shows an alternative embodiment of an ear protector. FIGS. 7-10 show alternative embodiments of sound damping filters, including those having membranes 5a, 5b, and 5c, as shown in FIGS. 7 and 9.

The detailed drawings, specific examples and particular formulations given, serve the purpose of illustration only. Furthermore, other substitutions, modifications, changes, and omissions may be made in the design, operating conditions, and arrangement of the exemplary embodiments without departing from the scope of the invention as expressed in the appended claims.

The invention claimed is:

1. Ear protector with a sound damping filter, comprising a membrane composed of a material for permitting the transmission of air with respect to the ear from the outside to the inside of the ear protector, wherein the membrane is composed of a material for permitting the transmission of air and water vapour with respect to the ear from the inside to the outside of the ear protector, the membrane being pre-stressed mounted in the sound damping filter, enabling a bigger membrane surface and hence bigger air and water vapour transport at the same sound attenuation.

2. Ear protector according to claim 1, wherein the membrane is pre-stressed mounted in the sound damping filter, enabling a 100-250% bigger membrane surface with respect to the original surface.

3. Ear protector according to claim 2, wherein the membrane is pre-stressed mounted in the sound damping filter, enabling a 150-200% bigger membrane surface with respect to the original surface.

4. Ear protector according to claim 1, wherein the filter comprises a filter housing, and the filter housing comprises a first and a second acoustic channel extending from one side of the housing to the other side, said second acoustic channel being designed for less attenuation of low frequencies.

5. Ear protector according to claim 1, wherein the sound damping filter comprises a support carrying the membrane, said support having standardized dimensions and being interchangeably mounted in a sound channel of the ear protector, connecting the inside and outside of the ear protector.

6. Ear protector according to claim 5, wherein the support carries membrane deflection limiters, located at both sides of the membrane.

7. Ear protector according to claim 6, wherein each of the membrane deflection limiters comprises an impulse blocker mesh.

8. Ear protector according to claim 6, wherein deflection of the membrane causes an opening in the sound channel to close.

9. Ear protector according to claim 1, wherein the membrane is composed of non-porous material enabling water vapour molecules to be transported through the membrane from the inside to the outside of the ear protector by way of absorption and evaporation processes and preventing the transmission of water from the outside to the inside of the ear protector.

10. Ear protector according to claim 9, wherein the non-porous material comprises polyester for molecular strength and polyether to transport water vapour molecules.

11. Ear protector according to claim 10, wherein the non-porous material comprises a thermoplastic polyurethane.

12. Sound damping filter for an ear protector according to claim 1, wherein the sound damping filter is a separate construction element.

13. A method for manufacturing a sound damping filter for an ear protector according to claim 1, said sound damping filter comprising a membrane composed of material permitting with respect to the ear from the inside to the outside of the ear protector the transmission of water vapour and of air, wherein the method comprises:
pre-stressing the membrane with a defined force,
placing the membrane pre-stressed in a mould, and
joining by injection moulding a support to the membrane.

14. A method for manufacturing a sound damping filter for an ear protector according to claim 1, said sound damping filter comprising a membrane composed of material permitting with respect to the ear from the inside to the outside of the ear protector the transmission of water vapour and of air, wherein the method comprising following steps comprises:
joining the membrane to a support and
pre-stressing the membrane by applying a specific treatment to introduce the required stress in the membrane.

15. The method of claim 14, wherein the treatment is heat treatment.

16. A method for manufacturing a sound damping filter for an ear protector according to claim 1, said sound damping filter comprising a membrane composed of material permitting with respect to the ear from the inside to the outside of the ear protector the transmission of water vapour and of air, wherein the method comprises:
joining the membrane to a support and
pre-stressing the membrane by applying a defined deformation of the membrane to introduce a required stress in the membrane upon assembly of the support of the membrane with another part of the ear protector.

17. The method of claim 16, wherein the other part of the ear protector is a housing of the filter or another support.

* * * * *